United States Patent [19]

Warning et al.

[11] Patent Number: 5,041,671

[45] Date of Patent: Aug. 20, 1991

[54] PROCESS FOR THE PREPARATION 4-CHLORO-2,5-DIMETHOXY-ANILINE

[75] Inventors: Klaus Warning, Eppstein/Taunus; Kurt Habig, Mörfelden-Walldorf, both of Fed. Rep. of Germany

[73] Assignee: Hoechst Aktiengesellschaft, Frankfurt am Main, Fed. Rep. of Germany

[21] Appl. No.: 369,290

[22] Filed: Jun. 21, 1989

[30] Foreign Application Priority Data

Jun. 22, 1988 [DE] Fed. Rep. of Germany ....... 3821013

[51] Int. Cl.$^5$ ........................................... C07C 209/36
[52] U.S. Cl. .................................................. 564/417
[58] Field of Search ....................................... 564/417

[56] References Cited

U.S. PATENT DOCUMENTS

| | | | |
|---|---|---|---|
| 3,145,231 | 8/1964 | Kosak | 260/580 |
| 3,803,054 | 4/1974 | Habig et al. | 564/417 X |
| 4,059,627 | 11/1977 | Kritzier et al. | 564/417 X |
| 4,070,401 | 1/1978 | Hirai et al. | 260/580 |
| 4,082,803 | 4/1978 | Paszthory et al. | 564/417 |

FOREIGN PATENT DOCUMENTS 2308105 8/1973 Fed. Rep. of Germany .
2156051 10/1974 Fed. Rep. of Germany .
1393428 5/1975 United Kingdom .

Primary Examiner—Richard L. Raymond
Assistant Examiner—P. O'Sullivan

[57] ABSTRACT

Process for the preparation of 4-chloro-2,5-dimethoxyaniline by catalytic reduction of 4-chloro-2,5-dimethoxynitrobenzene with hydrogen in the liquid phase at an elevated temperature and elevated pressure, which comprises carrying out the reduction at temperatures from about 80° to about 110° C. and under a pressure of about 5 to 50 atmospheres gauge in an aromatic solvent in the presence of a modified platinum-on-carbon catalyst in the presence of about 0.01 to about 0.2 mole of a compound which gives a pH of 8 to 10 in aqueous solution, and in the presence of about 0.1 to about 1.0% by weight of an aliphatic, open-chain, primary, secondary or tertiary amine or a cyclic amine, in each case relative to the amount in moles and weight, respectively, of 4-chloro-2,5-dimethoxynitrobenzene employed.

8 Claims, No Drawings

PROCESS FOR THE PREPARATION 4-CHLORO-2,5-DIMETHOXY-ANILINE

The invention relates to a process, improved compared with the state of the art (German Patent 2,156,051), for the preparation of 4-chloro-2,5-dimethoxyaniline by catalytic reduction of 4-chloro-2,5-dimethoxy-1-nitrobenzene.

In the process described in the German Patent quoted above the catalytic reduction of 4-chloro-2,5-dimethoxy1-nitrobenzene is effected in an aromatic solvent, for example xylene, in the presence of a modified platinum-on-carbon catalyst, within a temperature and pressure range from about 80° to about 110° C. and from about 5 to about 50 atmospheres gauge, respectively, and with the addition of buffer substances which show a pH range of 8 to 10 in aqueous solution. In order to obtain a base conforming to the standard, of good purity and having a pale appearance in a good yield, the catalyst must be filtered off each time under nitrogen and the xylene filtrate must be stirred under cold conditions for the deposition of the base (prior removal of the solvent and subsequent deposition of the base from water results only in dark products of unsatisfactory quality; in this regard, see Comparison Example 2). The virtually colorless 4-chloro-2,5-dimethoxyaniline which has crystallized out is then isolated by filtration and dried. The filtrate, which turns a red color in the course of the filtration can be employed several times in the reduction before purification by distillation has to be carried out.

It is a disadvantage in this procedure that the filtration of the base from the xylene filtrate is associated with losses of solvent which result in undesirable exit air problems. In addition, the base product which is at first obtained moist with xylene must still be freed from adhering solvent, which means an additional operation, either in the form of drying (by heat) or steam treatment of an aqueous base suspension moist with xylene.

It was therefore the object to carry out the reduction so selectively in that there is present, as soon as the reduction is complete, a base conforming to the standard, the isolation of which does not require, for final purification, any further crystallization from the xylene solution, but which can be obtained in a virtually quantitative yield as granules conforming to the standard, and directly from water, specifically after the removal of the aromatic solvent, for example xylene, by vacuum distillation or after the aromatic solvent (xylene) has been stripped off with steam.

This object is achieved in accordance with the invention by adding a suitable amine to the reduction mixture in catalytic amounts and in other respects following the process of German Patent 2,156,051 which has been quoted.

The present invention therefore relates to a process for the preparation of 4-chloro-2,5-dimethoxyaniline by catalytic reduction of 4-chloro-2,5-dimethoxynitrobenzene with hydrogen in the liquid phase at an elevated temperature and elevated pressure, by carrying out the reduction at temperatures from about 80° to about 110° C. and under a pressure of about 5 to about 50 atmospheres gauge, preferably about 10 to about 20 atmospheres gauge, in an aromatic solvent in the presence of a modified platinum-on-carbon catalyst, for example a sulfited or sulfided platinum-on-carbon catalyst, preferably a sulfited platinum-on-carbon catalyst, in the presence of about 0.01 to about 0.2 mole of a compound which gives a pH of 8 to 10 in aqueous solution, and in the presence of about 0.1 to about 1.0% by weight, preferably about 0.2 to about 0.5% by weight, of an aliphatic, open-chain, primary, secondary or tertiary amine or a cyclic amine, in each case relative to the 4-chloro-2,5-dimethoxynitrobenzene employed.

Amines of the general formulae below may be mentioned as examples of suitable aliphatic, open-chain amines

$$C_nH_{2n+1}-NH_2 \quad (1)$$
$[n = 1-6],$

$$H_2N-(CH_2)_m-NH_2 \quad (2)$$
$[m = 1-6],$ for example ethylenediamine or tetramethylenediamine, tetramethylenediamine being particularly effective,

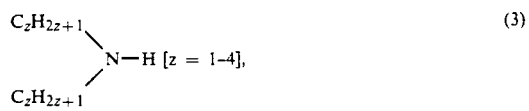

$$\begin{matrix} C_zH_{2z+1} \\ \phantom{C_zH_{2z+1}} \diagdown \\ \phantom{C_zH_{2z+1}\diagdown} N-H \; [z = 1-4], \\ \phantom{C_zH_{2z+1}} \diagup \\ C_zH_{2z+1} \end{matrix} \quad (3)$$

for example di-n-propylamine, and

$$N(C_pH_{2p+1})_3 \quad (4)$$
$[p = 1-4],$ for example tributylamine.

Examples of suitable aliphatic cyclic amines which may be mentioned are piperidine, piperazine and especially morpholine.

It is also possible to employ mixtures of the amines mentioned above.

The following may be mentioned as examples of suitable compounds which produce a pH of 8 to 10 in aqueous solution: disodium diborate, borax, sodium formate, sodium acetate, sodium carbonate, disodium hydrogenphosphate or sodium hydroxide. Instead of the sodium compounds mentioned as examples above, it is also possible to use the corresponding other alkali metal compounds, in some cases also the alkaline earth metal compounds. It is also possible to use mixtures of the compounds mentioned above.

Provided that the amine employed in accordance with the invention is sufficiently strongly basic, it is also possible for the amine employed to be used, instead of an inorganic compound having an alkaline reaction, to neutralize the hydrogen chloride or the hydrochloric acid formed therefrom which is liberated in a small amount (about 0.1% by weight) in the course of the reduction. In this case it can be necessary to employ the amine in a higher concentration than that indicated earlier in the text.

Examples of suitable aromatic solvents are benzene, chlorobenzene, dichlorobenzenes and trichlorobenzenes and mixtures thereof, ethylbenzene, cumene, preferably toluene and especially xylenes.

After the reduction is complete and after the catalyst has been filtered off, an organic filtrate is obtained from which, after the addition of water and after the removal (distillation under a slight vacuum or steam distillation under normal pressure) of the aromatic solvent (for example xylene), the base is, surprisingly, deposited on cooling in the form of virtually colorless, stable granules in a virtually quantitative yield.

It is known that the catalytic reduction of halogen-containing nitro-aromatic compounds in the presence of active, i.e. non-sulfided or non-sulfited, platinum-on-carbon catalysts and using morpholine or N-containing bases considerably reduces (0.1 to 0.5%) dehalogenation in the case of a series of chloronitrobenzenes and chloronitrotoluenes, but chloronitro-aromatic compounds containing alkoxy groups are not mentioned (U.S. Pat. No. 3,145,231, Annals New York Academy of Sciences 1986, pages 175–184). On the other hand, it was found in German Offenlegungsschrift 2,308,105 (Comparison Example 2 that the hydrogenation of 3,4-dichloronitrobenzene using 5% of Pt/carbon catalyst and in the presence of morpholine results in a 1% elimination of chlorine and additionally to 4% by weight of an unknown substance. The last result can perhaps also be applied to the reduction of chloronitroresorcinol dimethyl ether. This is because, under comparable reaction conditions, the chlorine elimination here is 1.5%, which is known to result in the undesirable formation of aminohydroquinone dimethyl ether; in addition other byproducts are formed (for example the formation of phenol by cleavage of the ether groups), which impart an intense blue-violet appearance to the base (see Comparison Example 1).

It is, therefore, entirely surprising that morpholine or the other amines employed in accordance with the process, added here in the form of a "co-catalyst" to an already modified, sulfided or sufited Pt/carbon catalyst, firstly reduce the elimination of halogen to $\leq 0.2\%$ and secondly, above all, prevent the formation of the strongly colored byproducts, so that the direct precipitation of chloroaminohydroquinone dimethyl ether from water is possible in a particularly elegant manner from the technical point of view.

In other respects essentially the same reaction conditions as those described in detail in German Patent 2,156,051, column 2, apply for carrying out the reduction.

The reduction is carried out by charging the nitro compound, aromatic solvent, catalyst, co-catalyst and the aqueous alkaline solution to the autoclave and, after expelling the air with nitrogen, heating the autoclave with stirring. Hydrogen is injected until no further decrease in pressure takes place. The desired reaction temperature is maintained by external cooling. When the reduction is complete the catalyst is filtered off under nitrogen, water is added and the solvent is removed by steam distillation or distillation under a slight vacuum and the base is precipitated in the form of granules from water by stirring under cold conditions. The granules are then filtered off in the form of a virtually colorless product and, if appropriate, are dried. This procedure also ensures that the catalyst can be recycled a very large number of times.

The process according to the invention enables 4-chloro2,5-dimethoxyaniline to be prepared in a simpler manner compared with the process known from German Patent 2,156,051, and for equally good yields and purity to be achieved.

4-Chloro-2,5-dimethoxyaniline is a valuable intermediate for the preparation of dyes and pigments.

The invention will be illustrated in greater detail by means of the following examples, without being limited thereto.

Example 1

239 g (1.1 mol) of 4-chloro-2,5-dimethoxynitrobenzene, 675 ml of xylene (technical), 3 g of 5% Pt/carbon, sulfited, as a 50% mixture with water, 1 g of morpholine, 3 g (0.02 mol) of disodium hydrogenphosphate and 30 ml of water are initially placed in a stainless steel autoclave equipped with a magnetic lifting device, a heating device and cooling.

After the autoclave has been closed and the air expelled by means of nitrogen, the reaction mixture is heated to 85° C. and hydrogen is injected with stirring up to a pressure of 10 bar. The reduction begins immediately with the formation of heat and a decline in the hydrogen pressure. The temperature is allowed to rise to 95° C. and is then kept at this level with cooling. The pressure is kept within a pressure range from 5 to 15 bar by injecting further hydrogen. When no more reduction in pressure takes place, stirring is continued for a further 30 minutes at 95° to 100° C. and under a pressure of 20 bar. On average, the whole reduction time is 60 minutes (compared with 75 minutes in the process of German Patent 2,156,051). After releasing the pressure, the catalyst is removed under nitrogen via a pressure filter at 95° C. and is recycled to the next reduction batch. 500 ml of water are added to the filtrate in a stirred flask, the xylene is removed by distillation with steam or under a slight vacuum (bottom temperature 90° to 100° C.) and the base is precipitated in the form of granules by stirring with cooling to 20° to 25° C. Filtration gives a virtually colorless 4-chloro-2,5-dimethoxyaniline, moist with water, which is insensitive to air and can, if appropriate, also be dried in a customary manner.

The aqueous filtrate has a pH of 8.2 and the xylene removed by distillation can be recycled to the next batch. The yield is 99% of theory; the solidification point is at least 117.8° C., the diazo value is $\geq 99\%$ and the content of aminohydroquinone dimethyl ether is $\leq 0.2\%$.

The same result is obtained if ethylenediamine, tetramethylethylenediamine or di-n-propylamine is employed instead of morpholine.

If di-n-butylamine or tri-n-butylamine is used, a slight increase in the elimination of chlorine (0.1 to 0.2%) is observed, the yield being virtually the same and the appearance pale.

Comparison Example 1

The reaction was carried out in accordance with Example 1, but with the difference that active 5% Pt/carbon catalyst was now employed instead of sulfited 5% Pt/carbon catalyst. The reduction time was 53 minutes. The yield was 94.2% of theory, the content of aminohydroquinone dimethyl ether was 1.5% and the pH of the aqueous filtrate 2.64. The base isolated had a blue-violet appearance and a solidification point of 115.9° C.

Comparison Example 2

The reaction was carried out in accordance with Example 1, but without the addition of morpholine or another amine. The reduction time was 60 minutes, the yield was 99% of theory and the content of aminohydroquinone dimethyl ether was 0.3 to 0.4%. The aqueous filtrate had a pH of 7.8 and the appearance of the base isolated was grey/slightly violet, solidification point 117.3° C.

We claim:

1. A process for the preparation of 4-chloro-2,5-dimethoxyaniline by catalytic reduction of 4-chloro-2,5-dimethoxynitrobenzene with hydrogen in the liquid phase at an elevated temperature and elevated pressure, which comprises carrying out the reduction at temperatures from about 80° to about 110° C. and under a pressure of about 5 to about 50 atmospheres gauge in an aromatic solvent in the presence of a sulfited or sulfided platinum-on-carbon catalyst, in the presence of about 0.01 to about 0.2 mole of a compound which gives a pH of 8 to 10 in aqueous solution, and in the presence of about 0.1 to about 1.0% by weight of an aliphatic, open-chain, primary, secondary or tertiary amine or a cyclic amine, in each case relative to the amount in moles and weight, respectively, of 4-chloro-2,5-dimethoxynitrobenzene employed.

2. The process as claimed in claim 1, wherein the reduction is carried out in the presence of an amine of the formula $$C_nH_{2n+1}-NH_2 \ [n = 1-6], \quad (1)$$

$$H_2N-(CH_2)_m-NH_2 \ [m = 1-6], \quad (2)$$

$$\begin{array}{c} C_zH_{2z+1} \\ \phantom{xx} \diagdown \\ \phantom{xxxxx} N-H \ [z = 1-4] \ \text{or} \\ \phantom{xx} \diagup \\ C_zH_{2z+1} \end{array} \quad (3)$$

$$N(C_pH_{2p+1})_3 \ [p = 1-4]. \quad (4)$$

3. The process as claimed in claim 1, wherein the reduction is carried out in the presence of piperidine, piperazine or morpholine.

4. The process as claimed in claim 1, wherein the reduction is carried out in the presence of tetramethylenediamine.

5. The process as claimed in claim 1, wherein the reduction is carried out in the presence of disodium hydrogenphosphate.

6. The process as claimed in claim 1, wherein the reduction is carried out in the presence of sodium hydroxide.

7. The process as claimed in claim 1, wherein the reduction is carried out in toluene or a xylene or a mixture of xylenes.

8. A process for the preparation of 4-chloro-2,5-dimethoxyaniline by catalytic reduction of 4-chloro-2,5-dimethoxynitrobenzene with hydrogen in the liquid phase at an elevated temperature and elevated pressure, which comprises carrying out the reduction at temperatures from about 80° to about 110° C. and under a pressure of about 5 to about 50 atmospheres gauge in an aromatic solvent in the presence of a sulfited platinum-on-carbon catalyst, in the presence of about 0.01 to about 0.2 mole of a compound which gives a pH of 8 to 10 in aqueous solution, and in the presence of about 0.1 to about 1.0% by weight of an aliphatic, open-chain, primary, secondary or tertiary amine or a cyclic amine, in each case relative to the amount in moles and weight respectively, of 4-chloro-2,5-dimethoxynitrobenzene employed.

* * * * *